Figure 1:
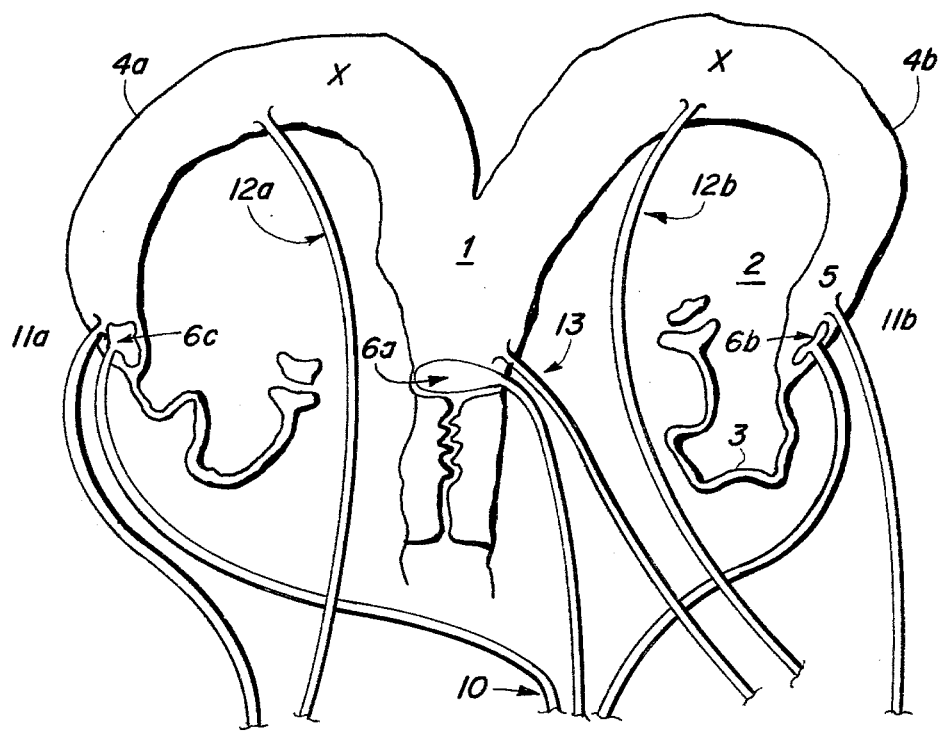

United States Patent [19]

Barnett

[11] 4,193,392

[45] Mar. 18, 1980

[54] METHOD FOR REMOVING OVA FROM ANIMALS

[76] Inventor: Gordon R. Barnett, Cape Rodney Farm, P.O. Box 95, Leigh, Warkworth, New Zealand

[21] Appl. No.: 836,106

[22] Filed: Sep. 23, 1977

[51] Int. Cl.² .................. A61B 19/00; A61M 25/00
[52] U.S. Cl. ................................. 128/1 R; 128/348
[58] Field of Search ............... 128/1 R, 2 B, 2 F, 348, 128/350 R, 276, 240, 241

[56] References Cited

U.S. PATENT DOCUMENTS

| 923,303 | 6/1909 | Shults | 128/344 |
|---|---|---|---|
| 2,493,326 | 1/1950 | Trinder | 128/344 X |
| 2,642,874 | 6/1953 | Keeling | 128/349 B |
| 2,935,068 | 5/1960 | Donaldson | 128/348 |
| 3,392,722 | 7/1968 | Jorgensen | 128/1 R |
| 3,515,124 | 6/1970 | Gurchot | 128/1 R |
| 3,540,451 | 11/1970 | Zeman | 128/348 X |
| 3,636,940 | 1/1972 | Gravlee | 128/241 X |
| 3,653,359 | 4/1972 | Tolle et al. | 119/14.02 |
| 3,866,598 | 2/1975 | Augspurger | 128/1 R |
| 4,004,588 | 1/1977 | Alexander | 128/241 |
| 4,102,342 | 7/1978 | Akiyama et al. | 128/344 X |

Primary Examiner—Dalton L. Truluck
Attorney, Agent, or Firm—Ladas, Parry, Von Gehr, Goldsmith & Deschamps

[57] ABSTRACT

A method and means for inserting fluid into a uterus of an animal is described. One or more inlet cannula lead into a uteral area and communicates with the exterior of the animal. Means for sealing off the uteral area is provided and one or more outlet cannula lead from the uteral area and communicate with the exterior of the animal. By this means, ova can be removed without the need for separate surgical operation. As described, the means for sealing off the uteral area consists of inflatable diaphragms.

1 Claim, 2 Drawing Figures

METHOD FOR REMOVING OVA FROM ANIMALS

This invention relates to an improved method and means for withdrawing ova and embryos from animals and/or artificial insemination.

Up until this time, it has been found that present surgical techniques for the withdrawal of ova from animals and relating to the transfer of ova from one animal to another, result in damage to valuable donor animals. In addition, the effect that such surgical techniques have on the animals has necessitated to a large extent the limitation of operations to a maximum of two or three operations in the lifetime of a donor animal.

It has also been found that there is a risk of permanent infertility from such operations and present surgical techniques have not always been totally effective.

Attempts have been made to flush ova from donor animals by inserting a flexible or part stiffened tube through the cervix and up into the uteral horn. This however, requires a great deal of skill if the uterus is to be flushed without damaging the tissue of the cervix or uterus, as not only is the cervix difficult to penetrate but in the case of animals with a bifurcated uterus it is difficult to ensure that the end of the tube reaches into the uteral horn. For example, cows have a bifurcated uterus, each horn of which is curved in a spiral fashion.

It is an object of this invention to go some way towards overcoming the abovementioned disadvantages in providing means for withdrawing ova from an animal, or which will at least provide the public with a reasonable choice.

According to one aspect of this invention there is provided means for inserting fluid into a uterus of an animal, including one or more inlet cannula leading to a uteral area and communicating with the exterior of the animal; means for sealing off said uteral area; and one or more outlet cannula leading from said uteral area and communicating with the exterior of the animal; so that in use, fluid can be inserted into said uteral area through one or more inlet cannula and thereafter withdrawn through one or more outlet cannula.

According to another aspect of this invention there is provided a method of inserting fluid into a uterus of an animal, including sealing off a uteral area; inserting fluid into said uteral area through at least one inlet cannula implanted in the animal; and thereafter withdrawing said fluid through at least one outlet cannula implanted in the animal.

This method can be used to insert fluid into said uteral area to displace ova, fertilised ova, or embryos, and to remove any displaced ova, fertilised ova or embryos, through the outlet cannula. Alternatively, or in addition, the fluid can include or be preceded by semen.

The invention will now be described by way of example only and with reference to the accompanying drawings, wherein:

FIG. 1: is a diagrammatic view of the uterus of a cow in conjunction with means for withdrawing ova in accordance with this invention.

Figure 2:
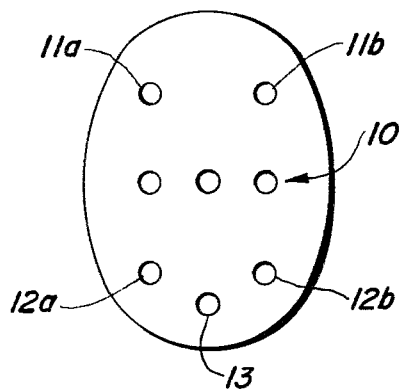

FIG. 2: illustrates a connection plate in accordance with this invention.

It should be appreciated that the present invention has particular application to all types of animals, such as for example cattle and the like, where it is desired to have rapid evolvement of new breeds. Additionally, it will be appreciated that while the invention may be described with reference to the removal of ovum, from an animal, the invention has equal application to the removal of embryos and fertilised ovum from within animals.

The present invention provides a method whereby a fluid can be inserted into at least one oviduct and/or the uterus of an animal, so as to cause any ovum located in either the oviduct or the uterus, to be flushed by the fluid, from the wall of either the oviduct or the uterus, so as to be mixed with and contained in the fluid. The fluid is preferably a suitable sterile fluid, of any known type or mixture.

In one form of the invention the fluid is inserted into the uterus at two or more positions simultaneously, so as to permit a slower flushing.

Alternatively, fluid can be inserted into, for example, the uteral area adjacent the oviducts and withdrawn from, for example, a position within or adjacent the uteral passage.

To facilitate performance of the present invention, means such as an intra-uterinary arrangement is inserted, surgically, into an animal (for example a breeding pedigree cow). The intra-uterinary arrangement (to be described hereinafter) can be inserted surgically during an operation, and is so inserted so as to remain positioned within the animal permanently, and so as to enable the animal to perform normal functions, without any inconvenience or irritation. It will be appreciated that this prevents or overcomes the necessity for a plurality of surgical operations during the life of the animal as has been known to take place up until this time.

FIG. 1 shows a diagrammatic view of the bifurcated uterus 1 of a cow. The upper uteral area 5 of each uteral horn 4a and 4b leads into oviducts 3 and ovaries 2.

In the form of the invention shown in FIG. 1 of the accompanying drawings, each upper uteral horn 5 is opened to permit the insertion of sealing means, which in the preferred form of the invention are in the form of inflatable diaphragms 6b and 6c, formed of a suitable material such as, for example, rubber, plastics or the like. A further diaphragm 6a is inserted into the lower uterus (adjacent the cervix as illustrated) and these diaphragms are inserted surgically, and have tubes or pipes formed of a suitable flexible material, running therefrom and to a position externally of the animal, such as for example externally of the abdominal area of the animal. In such an area there is little or no muscular movement and thus the least possible damage is done to the animal.

The tubes 10 passing from the diaphragms 6 to the position externally of the animal, have associated therewith means such as for example hand pumps and the like, which are able to be attached thereto, as that air may be pumped into the diaphragms to inflate them or to deflate them. It will be appreciated from the accompanying drawings, that once the diaphragms are inflated, the uteral area (such as X in FIG. 1) between the diaphragms 6 is sealed off. For the purpose of comparison, diaphragm 6b is shown to be deflated, whilst diaphragms 6a and 6c are shown to be inflated.

It will be recognised that diaphragm 6a could be replaced by extra diaphragms in each uteral horn to seal an area in each uteral horn.

Further tubing in the form of cannulas 11, 12 and 13 are installed in the uterus and communicate with a position externally of the animal. This permits a fluid, such as the sterile fluid referred to hereinbefore, to be inserted or flushed through one or more inlet cannula into the area X (defined by the inflated diaphragms 6), and for the fluid to be removed through one or more outlet cannula. It will be appreciated that on the sterile fluid being flushed into the upper uteral area X via inlet cannula 11, one or more ova (fertilised or unfertilised), or embryos, will be displaced from the wall of the uterus and will be carried by the fluid and can be withdrawn via outlet cannula 13 or intermediate cannula 12, in a straight forward and efficient manner.

If desired, only one diaphragm may be included or inserted into the animal, such as in the position adjacent to the cervix, (that is the diaphragm 6a shown in the inflated position in the lower uteral passage). This need not be an inflatable diaphragm as the lower uterus or anterior cervix could be permanently plugged in cases where ova are to be removed.

So that the invention can operate effectively and in a straight forward manner, the tubes leading to and from the diaphragms and the inlet and outlet cannula preferably exit from the animal in approximately the same area. In such cases, it is desirable that the tubing or cannula exit from an area where there is little or no muscular movement, such as for example, the abdominal area, or the area below the vulva. In this form of the invention the junction includes a plate 20 of a suitable inert material, and which is inserted or sewn into the skin of the animal in some suitable manner. The plate is provided with a plurality of exits and entry sockets passing therethrough, such that the tubing and cannula may be connected thereto and readily coupled to sources of air and fluid.

In use, an animal with means for removing ova inserted therewithin, is taken and the air inlet tubes connected to the plate are attached to a suitable air supply (for example a syringe, bulb, pump or the like), to inflate the diaphragms 6 and to therefore seal off the uteral area X of the animal. The inlet sterile fluid is pumped or passed into the inlet cannula so as to flush the upper uteral areas of the animal, to remove one or more ova or embryos therefrom. The outlet cannula are connected at the plate to suitable withdrawal means, such as for example syringes or the like, and the sterile fluid containing any ova or embryos is withdrawn from the animal. For example, fluid could enter through cannula 11, and be removed through cannula 12 and 13.

It will be appreciated that the inflation of the one or more diaphragms 6 permits the fluid to be held and operate within a confined area, and this prevents leakage and the like.

In order that the apparatus may function as an assistance to artificial insemination, it is to be appreciated that conceptual rates may be maximised by the introduction of semen directly into the uteral area by being pumped from the exterior junction or plate along the required inlet cannula. Semen would be injected via the required inlet cannula directly into the appropriate uteral area by pumping the semen along the cannula at the head of a measured amount of sterile fluid.

According to this mode of operation of the invention, such an artificial insemination technique may provide a fertilization rate which has previously been impossible, and for any ovum produced. It is to be appreciated that such very high fertilization rates could be achieved by either natural or super ovulation techniques.

According to the method of the operation of this invention as hereinbefore described, the implanted intra-uterinary device may be utilised for the extraction, of a fertilised ovum, a plurality of fertilised ova or an embryo fertilised naturally or by the utilisation of the invention according to the mode disclosed above. Each and every time that the apparatus is utilised.

The micro-location of ova or embryos and their subsequent separation from the carrying fluid, can be assisted by providing a static positively charged dye released in the embryo carrying liquid, for concentrated attachment to negatively charged embryo surfaces or vice versa. This would simplify the visual location of the embryo. Alternatively, a modified form of virus filter could be used to help locate the ova or embryos.

It is to be appreciated that alternative apparatus may be provided for the carrying out of the present invention, and it is to be appreciated that the method according to the present invention has particular advantages with regard to injected insemination at the time of the normal three week oestrus cycle of the animal in which the intra-uterinary device is located, followed by embryo flushing and collection. Using this technique it is possible to retrieve some 17 embryos for implant into recipient animals per year.

Furthermore, in conjunction with the possible use of super ovulation approximately quarterly, then embryo extraction may be increasable to 50 or more embryo for recipient transfer annually.

Of course it is to be appreciated that whilst the advantages and examples described herein are related to cows, the invention may be applied to any other such animal, by the suitable adaption of the apparatus for performing the method of the present invention as disclosed herein.

Furthermore, the apparatus disclosed for the performance of the invention has been described by way of example only; modifications, alterations and additions may be made thereto without departing from the scope of this invention as set forth in the claims. The claims form part of this disclosure.

I claim:

1. A method of repeatedly flushing ova from the uterus of an animal including the steps of:
   (a) surgically implanting in the uterus at least one inlet cannula extending from the uterus to the exterior of the animal;
   (b) surgically implanting in the uterus at least one outlet cannula extending from the uterus to the exterior of the animal;
   (c) surgically implanting in a lower region of the uterus an inflatable diaphragm, and surgically implanting an inflation tube passing from the inflatable diaphragm to the exterior of the animal;
   (d) inflating said diaphragm prior to inserting a flushing fluid through said inlet cannula and withdrawing said flushing fluid through said outlet cannula to thereby withdraw an ovum or ova from the uterus;
   (e) deflating said diaphragm after flushing has been completed; and
   (f) repeating steps (d) and (e) each time it is desired to flush an ovum or ova from the uterus.

* * * * *